United States Patent [19]
Xiao et al.

[11] Patent Number: 5,821,546
[45] Date of Patent: Oct. 13, 1998

[54] METHOD AND SYSTEM FOR FECAL DETECTION

[75] Inventors: Min Xiao; Da Kui Zhuang; Guolu Zheng, all of Fayetteville; Michael F. Slavik, Springdale, all of Ark.

[73] Assignee: Board of Trustees of the University of Arkansas, Little Rock, Ark.

[21] Appl. No.: 748,271

[22] Filed: Nov. 13, 1996

[51] Int. Cl.$^6$ .................................................. G01N 21/64
[52] U.S. Cl. ..................... 250/458.1; 250/461.2; 250/459.1
[58] Field of Search ............................ 250/461.2, 461.1, 250/458.1, 459.1, 910, 359.1

[56] References Cited

U.S. PATENT DOCUMENTS

| | | | |
|---|---|---|---|
| 3,067,328 | 12/1962 | Harrison | 250/71 |
| 4,622,469 | 11/1986 | Akiyama | 250/458.1 |
| 5,474,910 | 12/1995 | Alfano | 435/34 |
| 5,621,215 | 4/1997 | Waldroup et al. | 252/461.2 |

*Primary Examiner*—Don Wong
*Attorney, Agent, or Firm*—Gilbreth & Strozier, P.C.; J.M. Mark Gilbreth; Robert W. Strozier

[57] ABSTRACT

A method of and apparatus for detecting the presence of fecal or ingesta matter contaminants on a poultry or meat item. The poultry or meat is exposed to excitation light of a selected bandwidth(s) and certain bandwidth(s) is(are) measured and compared to a threshold, above which indicates contaminants. Suitable excitation bandwidth and measuring bandwidth are selected such that the ratio of or difference between the resulting sample fluoresence and contamination fluoresence are greater then a certain ratio or difference. If contaminants are present, a controller can generate a signal and/or send the contaminated items to a wash station.

4 Claims, 7 Drawing Sheets

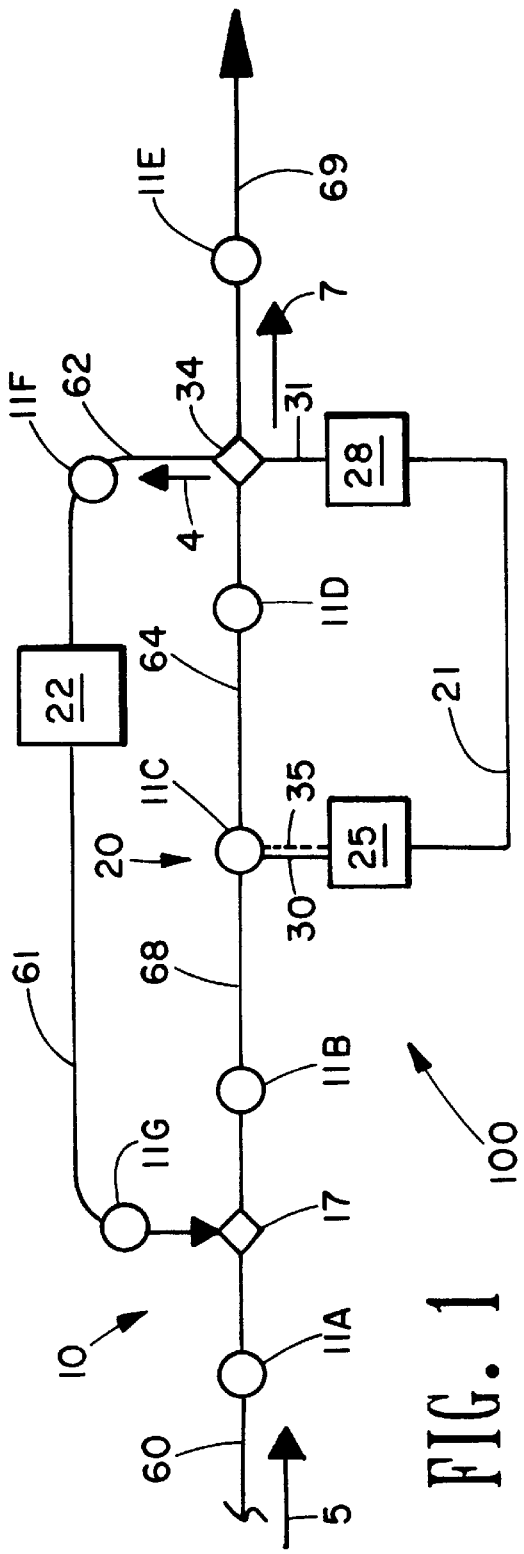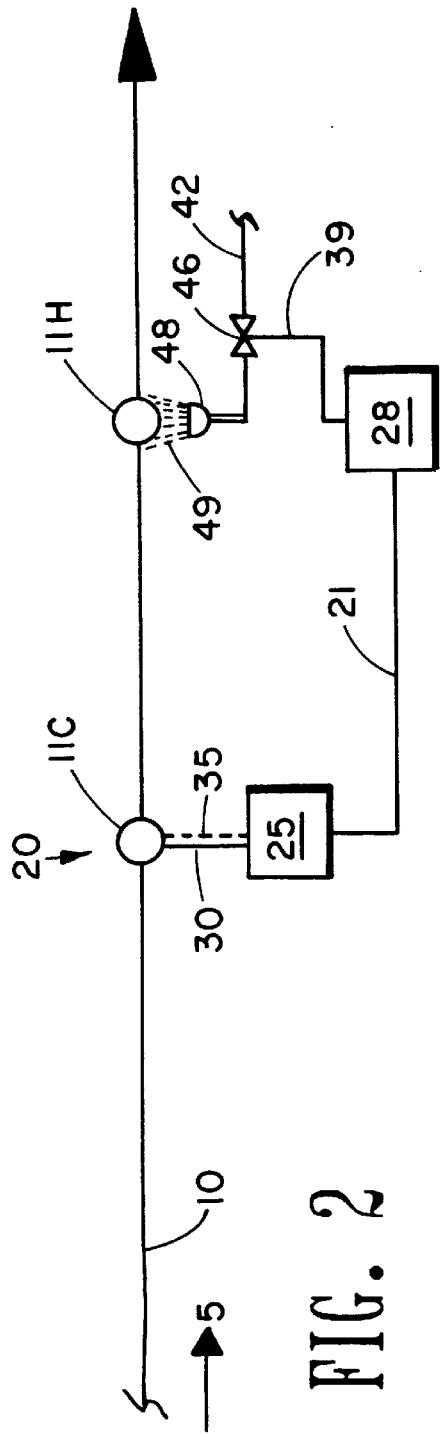

METHOD AND SYSTEM FOR FECAL DETECTION

BACKGROUND OF THE INVENTION

1. Field of the Invention

The present invention relates to a method of and system for detection contaminants. In another aspect, the present invention relates to a method of and system for detection of contaminants during the processing of foods or beverages. In even another aspect, the present invention relates to a method of and system for detection of fecal and ingesta material during the processing of poultry, beef, veal, pork, lamb and mutton. In still another aspect, the present invention relates to a method of and system for detection of contaminants utilizing fluorescence. In still another aspect, the present invention relates to a method of and system for detection of contaminants, wherein both the sample and contaminant are subject to fluorescence.

2. Description of the Related Art

Processing of meats and poultry, such as chicken, turkey, beef, veal, pork, lamb, mutton, and even the more exotic emu and ostrich, tend to expose them to fecal and ingesta matter. This is especially true when meats and poultry are processed utilizing highly automatic and rapid systems which might cut into or tear apart the intestines and bowels of those animals. Additional exposure to fecal matter occurs as a matter of course either during the raising of these animals in less than sanitary conditions, or from having these animals confined immediately prior to slaughter in holding pens.

Inspection of meat and poultry has always been of great importance to insure the safety of the food system. However, in spite of the importance of having proper inspections, the advances in meat and poultry inspection technology have been limited at best.

Recent meat contamination events involving e coli bacteria, more specifically the pathogenic e coli 0157:H7, have led the pubic and media to require more careful inspection of meat and poultry. Such publicity has also revealed to the public that inspection for bacterial contamination is many times conducted by a meat inspector using human sight to find microscopic bacteria and other contaminants. While such visual inspection techniques might reveal those meat and poultry carcasses in the advanced stages of contamination, or having pathogenic lesions and larger fecal material, they are not very efficient at finding less advanced stages of bacterial contamination, or microscopic amounts of fecal contamination.

With modern processing equipment and the economic demands of the market place, meat and poultry lines are typically run as quickly as possible, further complicating the task of human visual inspection.

There have been suggestions in the prior art for methods of inspecting foodstuffs.

Foods and feeds have natural components which fluoresce when exposed to energy at particular wavelengths. For example, coumarins, coumarosteroids, carotenoids, chlorophyllins, and other plant and animal pigments all have characteristic absorption and fluorescent properties. Fluorescence is commonly used to detect mouse and rat droppings in grain products, to detect the presence of *Aspergillus flavus* in various grain products, and to detect the spoilage organism, Pseudomonas in coolers and freezers.

U.S. Pat. No. 3,067,328, issued Dec. 4, 1962 to Harrison, discloses a method for the inspection of crustaceans to determine their freshness. The method involves exposing the shrimp to light in the violet and ultraviolet region of the spectrum of 250 to 375 millimicrons, and comparing the resultant fluorescence pattern against the bright white pattern for fresh shrimp.

U.S. Pat. No. 4,622,469, issued Nov. 11, 1986 to Akiyama, discloses a method of and apparatus for detecting rotten albumen. The apparatus includes a device for casting 300 to 410 nm UV light onto the albumen, an optical filter system for filtering out UV light at wavelengths less than 400 nm, and a discriminating means which compares the received signal to a predetermined threshold level of fluorescence from sound albumen, and after the comparison outputs a signal indicating the presence or absence of rotten albumen.

U.S. Pat. No. 5,474,910, issued Dec. 10, 1995 to Alfano, discloses a method and device for detecting fluorescent biological microorganisms or microorganisms containing such fluorescent biological molecules. The method includes illuminating with light of a suitable wavelength to excite the fluorescent biological molecules and then measuring the resultant light at a wavelength indicative of fluorescence of the fluorescent biological molecules.

However, in spite of these advancements in the prior art, none of these prior art references disclose or suggest a method of or apparatus for using fluoresence for inspecting a sample where both the sample and the contaminants fluoresce.

Thus, there is another need in the art for a method of or apparatus for using fluoresence for inspecting a sample where both the sample and the contaminants fluoresce.

There is another need in the art for an improved method of or apparatus for inspecting foodstuffs or beverages.

There is even another need in the art for an improved method of or apparatus for inspecting meats or poultry.

There is still another need in the art for a method of or apparatus for using fluoresence for inspecting foodstuffs or beverages for contaminants where both the foodstuff or beverages and contaminants fluoresce.

There is still another need in the art for a method of inspecting meats or poultry for contaminants where both the meats or poultry and contaminants fluoresce.

There is still another need in the art for a method of and apparatus for matching an unknown sample specimen to a known control using fluorescence.

These and other needs in the art will become apparent to those of skill in the art upon review of this specification, including its drawings and claims.

SUMMARY OF THE INVENTION

It is an object of the present invention to provide for a method of or apparatus for using fluoresence for is inspecting a sample where both the sample and the contaminants fluoresce.

It is another object of the present invention to provide for an improved method of or apparatus for inspecting foodstuffs or beverages.

It is even another object of the present invention to provide for an improved method of or apparatus for inspecting meats or poultry.

It is still another object of the present invention to provide for a method of or apparatus for using fluoresence for inspecting foodstuffs or beverages for contaminants where both the foodstuff or beverages and contaminants fluoresce.

It is yet another object of the present invention to provide for a method of inspecting meats or poultry for contaminants where both the meats or poultry and contaminants fluoresce.

It is even still another object of the present invention to provide for a method of and apparatus for matching an unknown sample specimen to a known control using fluorescence.

These and other objects of the present invention will become apparent to those of skill in the art upon review of this specification, including its drawings and claims.

According to one embodiment of the present invention there is provided a method of analyzing a sample for contaminants. The method includes shining light of a selected wavelength or range of wavelengths onto the sample. Next, the method includes gathering light of a specific wavelength or range of wavelengths fluorescing from the sample. The method also includes producing a signal indicative of the presence of contaminants if the gathered light has fluorescence intensity greater than a target threshold. The target threshold intensity value is set to be the fluorescence intensity for the sample in an uncontaminated state at the excition wavelength.

According to another embodiment of the present invention there is provided an apparatus for detecting the presence of contaminants. The system generally includes a conveyer system for moving the sample item along a pathway. The system also includes a light transmitter positioned adjacent the path to transmit light of a selected wavelength or range of wavelengths onto the sample item as it passes by the transmitter. The system additionally includes a light receiver for gathering light of a certain wavelength or range of wavelengths fluorescing from the sample. The system still additionally includes a processor for comparing the intensity of the fluorescent light gathered against a threshold fluorescence intensity. The target threshold intensity value is set to be the fluorescence intensity for the sample in an uncontaminated state at the excition wavelength. As separate optional embodiments, the system may also include a signal generator for generating a signal indicative of the presence of contaminants if the intensity of the florescent light gathered is greater than a threshold fluorescence, and/or for generating a signal indicative of the absence of contaminants if the fluorescent light gathered is less than a threshold fluorescence. The system may also include a wash system that either washes or sprays the contaminated sample.

According to even another embodiment of the present invention, there is provided a method for comparing a contaminated consumable sample to known controls. The method generally includes providing an excitation light having an excitation wavelength to the sample to produce sample fluorescence, with the light utilized is suitable to fluoresce the contaminant at a measurement wavelength. The next step includes measuring the sample fluorescence at the measurement wavelength. The resulting sample fluorescence spectrum is then compared to the fluorescence spectrum of the known controls.

BRIEF DESCRIPTION OF THE DRAWINGS

FIG. 1 is a schematic representation of one embodiment of inspection system 100 of the present invention, showing conveyer line 10, UV light transmitter/receiver 25, computer controller 28, switching station 34, and rewash station 22.

FIG. 2 is a schematic representation of another embodiment of inspection system 100 the present invention, showing conveyer line 10, UV light transmitter/receiver 25, computer controller 28 and rewash sprayer 48.

DETAILED DESCRIPTION OF THE INVENTION

Figure 3:
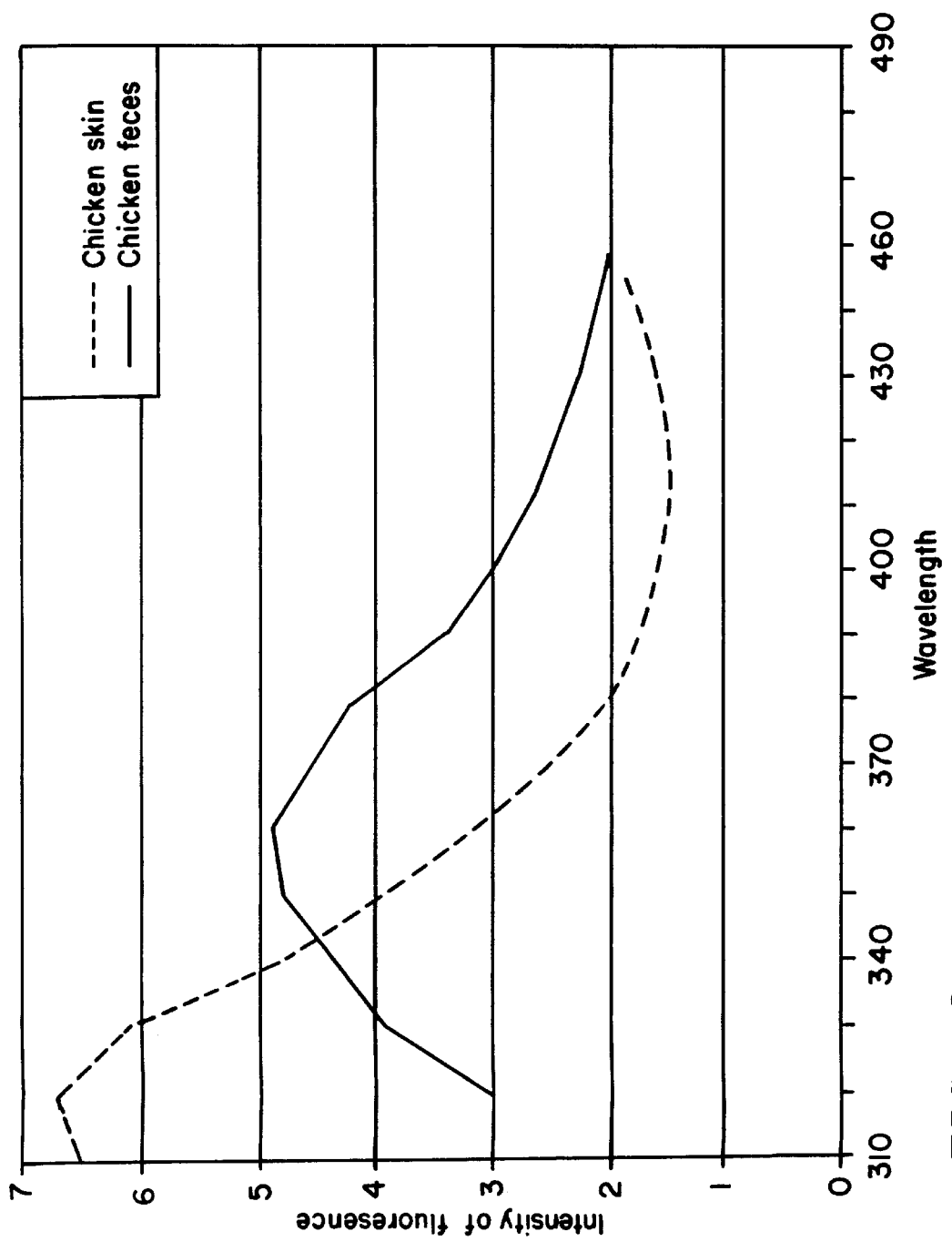
FIG. 3 is a graph showing fluorescence spectra of chicken skin and of feces, respectively when excited by light at a wavelength of 275 nm.

The method of the present invention generally includes exposing a sample to light of a selected wavelength or range of wavelengths, determining if the resultant fluorescence is indicative of presence of contaminants, and generating a signal to report, rewash or otherwise reject the sample.

As used herein, "foods" or "foodstuffs" are to be taken to refer broadly to meat, poultry, vegetables, fruits, grains, or dairy products, and to any product derived from or containing any of the foregoing.

"Meat" as used herein is to be taken to refer broadly to food products derived from livestock or game animals, including the following nonlimiting examples of beef, pork, veal, lamb, mutton, rabbit, venison, boar, and the like. "Poultry" as used herein is to be taken to refer broadly to food products derived from birds, including the following nonlimiting examples of chicken, turkey, pheasant, duck, quail and even the more exotic emu and ostrich. The present invention is preferably utilized to process turkey and chicken, most preferably chicken.

As used herein, "beverage" is to be understood to be any type of drink, nonlimiting examples of which include water, teas, juices, coffees, carbonated drinks, drinks from water and powders or syrups, wines, or beers.

As used herein, "consumables" refers to both beverages and foodstuffs.

"Contaminants" refers to bacteria, bacterial related matter or by-products, and fecal and ingesta matter.

The present invention is generally utilized to analyze consumables for the presence of contaminants. Preferably, the present invention is utilized to analyze foods for the presence of contaminants. More preferably, the present invention is utilized to analyze meats for the presence of contaminants. Even more preferably, the present invention is utilized to analyze poultry for the presence of contaminants. Most preferably, the present invention is utilized to analyze poultry for the presence of fecal or ingesta matter.

While not wishing to be limited by theory, it is believed that one or more components in poultry feces and in excreta from the crop of broilers (chicken), are fluorescent under light of certain wavelength or range of wavelength. These components are believed to be carotenoids or retinoids, or some other component related to the feed.

The present invention will now be further described by reference to FIGS. 1 and 2. It must be noted that while in FIGS. 1 and 2, the present invention is generally illustrated by reference to chicken contaminated with fecal or ingesta matter, the invention is not so limited and finds utility in analyzing any type of food or beverage for the presence of a contaminant.

Referring first to FIG. 1, there is shown one embodiment of system 100 of the present invention, showing conveyer line 10, light transmitter/receiver 25, computer controller 28, merge station 17, switching station 34, and rewash station 22.

In FIGS. 1 and 2, items 11A–H will be referred to as chicken 11, although it is to be understood that item 11 could be any foodstuff or beverage, including those described above, Chicken 11A–H progresses along conveyer system 10 in the general direction of arrow 5 as shown.

Chicken 11A is shown as entering conveyer system 10 on conveyer section 60. Conveyer systems are well known in the art of processing food and beverages. In the practice of the present invention, the specific type of conveyer system 10 is not critical. Thus, any suitable system may be utilized as conveyer system 10.

Chicken 11G is returning on conveyer section 61 from rewash station 22 where it was subjected to additional washing after fecal or ingests material was detected. Chicken 11G will return to conveyer portion 60 via merging station 17.

Chicken 11B is shown approaching, and chicken 11C is shown in detection area 20 where light 35 is transmitted by light transmitter/receiver 25 onto the chicken to be inspected. The resulting fluorsecent light 30 is received by light transmitter/receiver 25.

In the practice of the present invention, the wavelength or band of wavelength of excitation light utilized must be suitable to cause fluorescence upon striking the contaminant, which fluorescence must be sufficient for detection.

In some instances, both the sample and the contaminant will fluoresce when exposed to the excitation light. The relative intensities of the fluorescing sample and the fluorescing contaminant will vary depending upon the wavelength of the excitation light provided, and upon the measured wavelength. Thus, it is possible for the sample fluoresence to obscure the contaminant fluoresence. Therefore, both the wavelength or band of wavelength of the excitation light provided to the sample, and the wavelength or band of wavelengths to be measured of the fluorescing light, are selected so as to allow the detection of contaminants. This is accomplished by measuring fluoresence spectra of the sample and the contaminant separately for various excitation wavelength or wavelength band, and from the resulting fluorescence spectra, selecting a suitable excitation wavelength or band of wavelengths, and selecting a suitable wavelength or band of wavelengths to measure, such that the resulting ratio of contaminant fluoresence to sample fluoresence or the difference between the contaminant fluoresence and sample fluoresence, allows for detection of the contaminant.

For example, referring now to FIG. 3, there is shown fluorescence spectra of chicken skin and of feces when excited by 275 nm light. It should be understood that with most equipment, there is generally a bandwidth for the produced light, which for the embodiment shown is 1 to 3 nm. Generally, for the selected wavelength of excitation light, measurements are taken at that wavelength or range of wavelengths providing a sufficient ratio or difference between the intensities of the fluorescing contaminant ($I_{FC}$) to the fluorescing sample ($I_{FS}$) which will allow for discernment between the sample and the contaminant. Ideally, although not necessary, the excitation wavelength and the measurment wavelength are selected such that the ratio or difference between the intensities of the fluorescing contaminant ($I_{FC}$) to the fluorescing sample ($I_{FS}$) are maximized. This will occur if the minimum sample fluoresence intensity and the maximum contaminant fluoresence intensity occur at the same measured wavelength. While not necessary, it is preferred that the excitation wavelength and the measurment wavelength be selected such that the intensity of the fluorescing contaminant ($I_{FC}$) is greater than the intensity of the fluorescing sample ($I_{FS}$).

Generally, the ratio between the intensities of the fluorescing contaminant to the fluorescing sample will be at least about 0.000001. Preferably, the ratio between the intensities of the fluorescing contaminant to the fluorescing sample will be at least about 0.001, more preferably at least about 0.1, more preferably at least about 0.5, even more preferably at least about 1, and most preferably at least about 2. For example, referring again to FIG. 3, at 400 nm, the contaminant (chicken feces) intensity is about 3.0 and the sample (chicken skin) intensity is about 1.6, for a ratio of 1.875. At 380 nm, the contaminant (chicken feces) intensity is about 4.2 and the sample (chicken skin) intensity is about 2, for a ratio of 2.1.

Generally, the excitation wavelength and the measurement wavelength are selected such that the difference between the intensities of the fluorescing contaminant and the fluorescing sample are greater than any difference produced by experimental error or "noise" in the detection system. For example, if the measured intensities of fluorescence from the consumable samples tend to vary by a certain Δ, then the minimum difference between the intensities of the fluorescing contaminant and the fluorescing sample must be greater than this Δ. Generally, the excitation wavelength and the measurement wavelength are selected such that the difference between the total fluorescence intensity from the contaminated sample ($I_{FC}+I_{FS}$) and the fluorescence intensity of the uncontaminated sample ($I_{FS}$) (including the "noise" variation Δ) is at least 0.000001 times of fluorescence intensity of the uncontaminated sample $I_{FS}$. Preferably, the difference between the intensities of the fluorescening contaminated sample $I_{FC}+I_{FS}$ and the fluoresening uncontaminated sample $I_{FS}$ will be at least about 0.001 $I_{FS}$ will be at least about 0.001 $I_{FS}$, more preferably at least about 0.01 $I_{FS}$, at least about 0.1 $I_{FS}$, at least about 0.5 $I_{FS}$.

Figure 5:
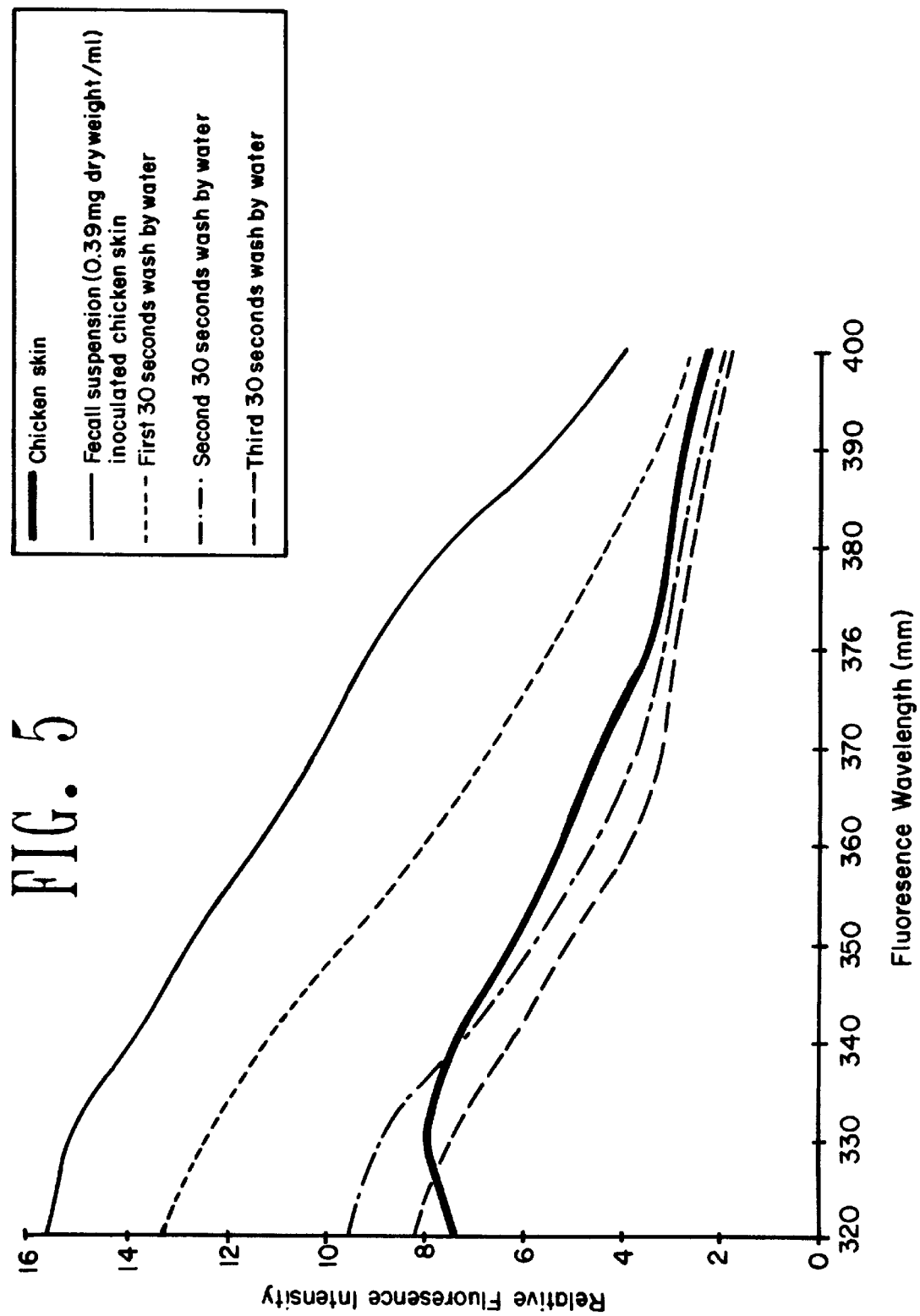
FIG. 5 is a graph of fluoresence spectrum of chick skin, fecal-water-suspension-inoculated chicken skin, and after a first, second and third 30 second water wash.

For example, referring to FIG. 5, at 400 nm, the total fluorescence intensity ($I_{FS}+I_{FC}$) is about 4.0 and the consumable (chicken skin fluorescence intensity $I_{FS}$ is about 2.0, for a difference of 2.0. At 380 nm, the total fluorescence intensity is about 7.5 and the consumable (chicken skin) fluorescence intensity is about 3.0, for a difference of 4.5. Notice that al these are measured using relative intensities.

Generally, any suitable wavelength of light may be utilized as the excitation light, provided that in the resulting fluorescing spectra, at least one wavelength or range of wavelength exists to provide a sufficient ratio or difference between the intensities of the fluorescing contaminant ($I_{FC}$) and the fluorescing sample ($I_{FS}$) which will allow for discernment between the sample and the contaminant. Generally, this means that the wavelength of light transmitted by transmitter 25 will be in the range of about 190 nm to about 850 nm, and the wavelengh received by receiver 25 will be in the range of about 200 nm to about 25,000 nm.

Selection of the suitable excitation wavelength will also depend upon the fluoresence nature of the sample and the contaminant. For example, for the detection of fecal contamination on chicken, the preferred wavelength of light transmitted by transmitter/receiver 25 will be in the range of about 210 nm to about 500 nm. Within in this range, there are more preferred ranges of about 260 nm to about 280 nm, about 340 nm to about 350 nm, 360 nm to about 370 nm, and about 390 nm to about 400 nm.

Once the excitation wavelength and the measurement wavelength are determined, the threshold intensity is equal to the intensity of the sample. For example, referring again to FIG. 3, at 400 nm, the contaminant (chicken feces) intensity is about 3.0 and the sample (chicken skin) intensity is about 1.6, for a threshold of 1.6. At 380 nm, the contaminant (chicken feces) intensity is about 4.2 and the sample (chicken skin) intensity is about 2, for a threshold of 2.

While the embodiment of the present invention is illustrated in FIG. 1 as having one instrument, light transmitter/receiver 25, for both the generation of light and for light gathering, it is to be understood that the invention is not so limited and that dedicated transmitters and receivers could be utilized. The received light 30 generates a signal 21 which is relayed to computer or controller 28.

Additionally, while the present system 100 is illustrated as having one transmitter and one receiver, it is envisioned that any suitable number of transmitter and receivers may be utilized. In fact, to cover a greater percentage of the surface area of the chicken, and thus increase the quality of the inspection, it is preferred that two or more transmitters and receivers be utilized.

It is also anticipated that work environment light, meaning the sun or artificial light, might cause some fluoresence which is detected by the receiver. Optionally, it is proposed that the excitation light be subjected to frequency, amplitude or phase modulation, which modulation is utilized to separate the desired fluoresence from the work environment light fluoresence using various correlation techniques.

The fluorescent light 30 may be received by any suitable receiver. Preferably the receiver 25 is a camera type device which will digitize received signal 30 for processing. Most preferably, a signal pixel width camera will be utilized.

Computer or controller 28 will compare the received wavelength against a threshold value as discussed above to determine if contaminants are indicated.

Chicken 11D is shown as approaching switching station 34 which is controlled by computer 28. For chicken which were indicated as having fecal or ingesta material, i.e., chicken 11F, computer 28 provides a signal via connection 31 to switching station 34 to route the chicken to rewashing station 22 on alternative pathway conveyer 64. Of course, while the present invention is illustrated in terms of a rewashing for chicken indicating presence of fecal or ingesta matter, it is to be understood that another alternative is to discard or manually process the chicken.

For chicken which were indicated as not having fecal or ingesta material, i.e., chickens 11E, computer 28 provides a signal via connection 31 to switching station 34 to route the chicken to conveyer 69 to continue for further processing.

After rewashing at rewashing station 22, the chicken then travels via conveyer 61 to merging station 17 to rejoin conveyer section 68.

Referring now to FIG. 2 there is shown a schematic representation of another embodiment of system 100 of the present invention, having conveyer line 10, fluoresence transmitter/receiver 25, computer controller 28 and rewash sprayer 48.

Chicken 11C is shown in detection area 20 where excitation light 35 is transmitted by light transmitter/receiver 25 onto the chicken to be inspected and thus causing fluorescence. Fluorescing light 30 is received by light transmitter/receiver 25.

Again, computer 28 will compare the received wavelength against a threshold value to determine if fecal or ingesta matter is indicated. For chickens which were indicated as having fecal or ingesta material, i.e., chicken 11H, computer 28 provides a signal via connection 39 to open valve 46 of wash line 42, to provide cleaning spray 49 through nozzle 48. Any suitable number of wash sprays can be arranged around chicken 11H.

Alternative embodiments of the apparatus of the present invention may be envisioned.

Figure 6:
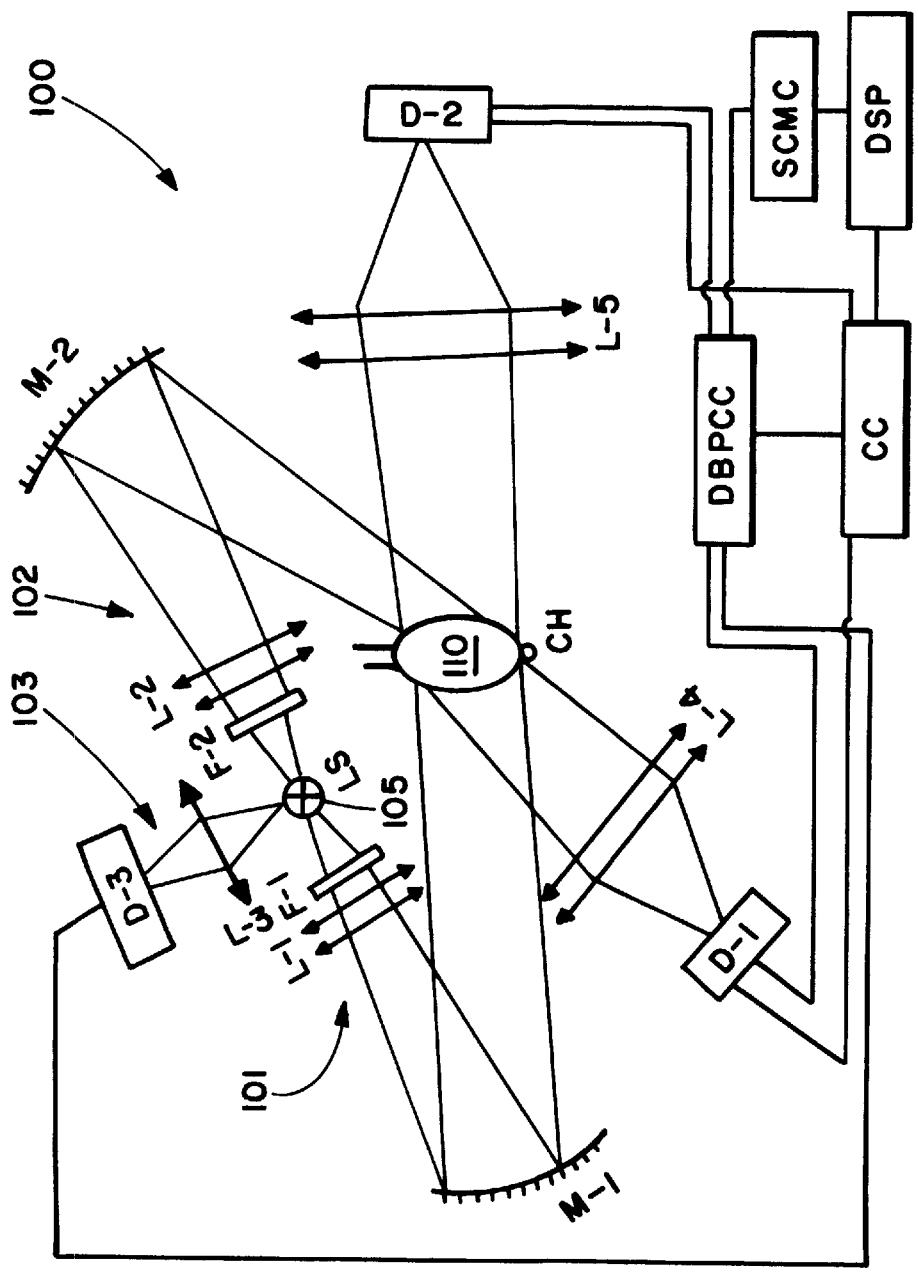
FIG. 6 is a schematic of one embodiment 100 of the present invention having three optical beams 101, 102 and 103, all emanating from light source (LS) 105, which are utilized to analyze target 110 for contaminants.

Referring now to FIG. 6, there is shown an a schematic of an embodiment 100 of the present invention having three optical beams 101, 102 and 103, all emanating from light source (LS) 105. Optical beams (L1) 101 and (L2) 102 are the excitation light sources which, after being subjected to optional modulation, have the same or different working frequencies. The third beam (L3) 103 passes through lens (L3) to a detector (D3) is used for monitoring the irradiation-intensity of the light source (LS) 105, and for normalization with the two excitation lights 101 and 102. Optical beams 101 and 102 are directed through filters (F1 and F2) and lens (L1 and L2) and focused by mirrors (M1 and M2) to target (CH or chicken) 110. Target 110 is excited by the selective wavelength, achieved by narrow band filters and the resulting fluorescence is demodulated after it is selectively (filtered through narrow band filters) received by the corresponding detector (D1 or D2). Other components include the double beam pass compensator (DBPCC), control equipment (CC), self-correlation measure component (SCMC), and data storing and processing (DSP).

Figure 7:
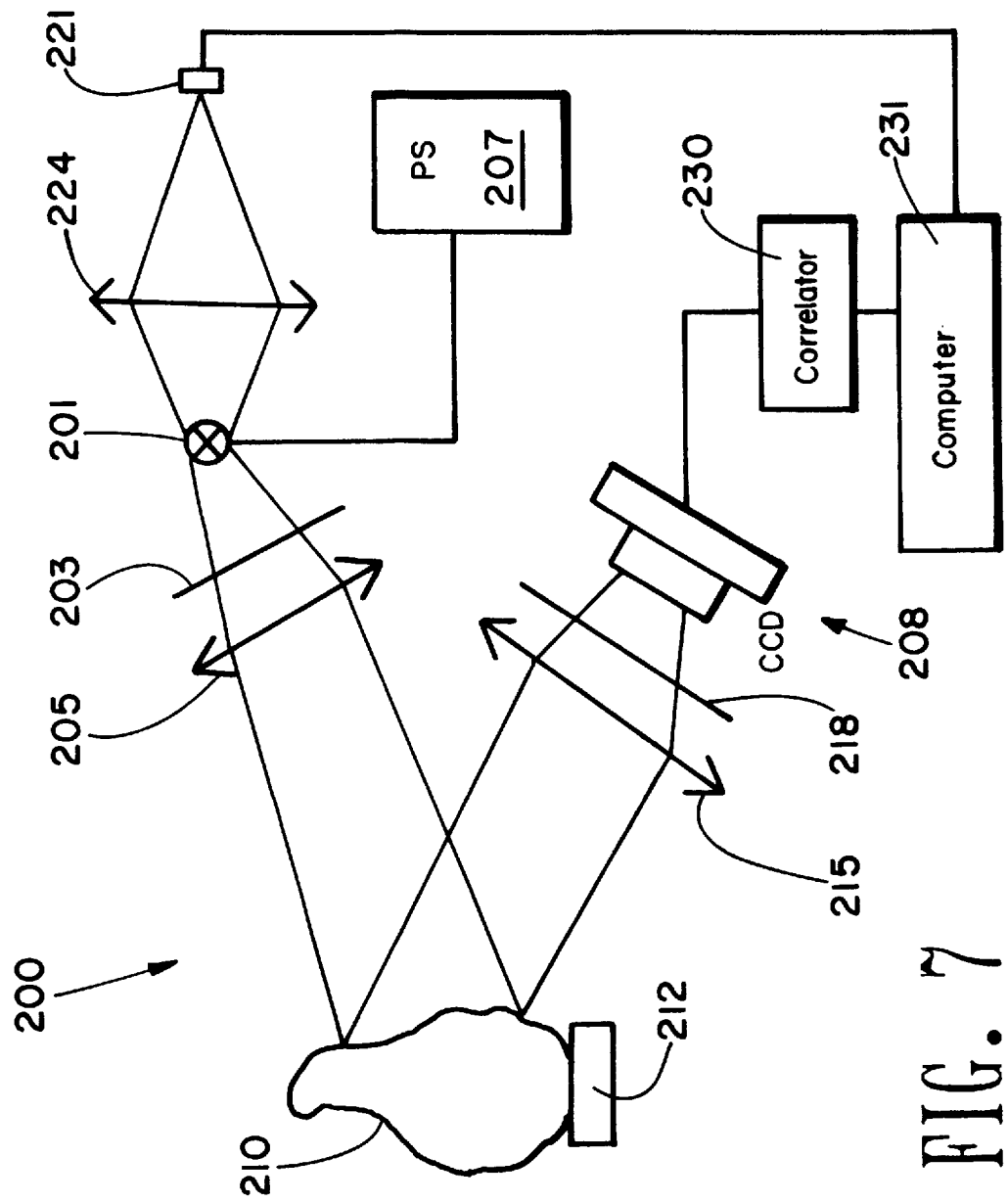
FIG. 7 is a schematic of one embodiment 200 of the present invention in which light source 201 directs excitation light through filter 203 and lens 205 to target 210, with fluorescing light travelling through lens 215 and filter 218 to detector 208.

Referring now to FIG. 7, there is shown another embodiment of the present invention. As shown in FIG. 7, this system 200 with power source 207 utilizes a modulated light source (LS) 201 with power source 207 focused by lens 205 onto target, the light wavelength is selected by filters (F) 203 or other dispersive elements, a two-dimensional imaging system 208 by using lens 215 and a charge-coupled device (CCD), and an optional rotating target holder 212. Again, the resulting fluorescence from the target (T) 210 is selectively received through optical filters (F) 218, focused by lens (L) 215, or other dispersive optical elements, and the resultant image forms in the CCD. Correlation is obtained by using modulation and demodulation techniques. Also included are detector 221, and then to computer 231.

The present invention can also be utilized for analyzing for very low levels of contamination in water. For example, as little as 0.000001 mg/l feces in water can be detected using the present invention. Thus, the presence of chicken-feces pollution in water can be determined for environments such as lakes, rivers, reservoirs, plant process streams, drinking water sources, and the like.

Figure 8:
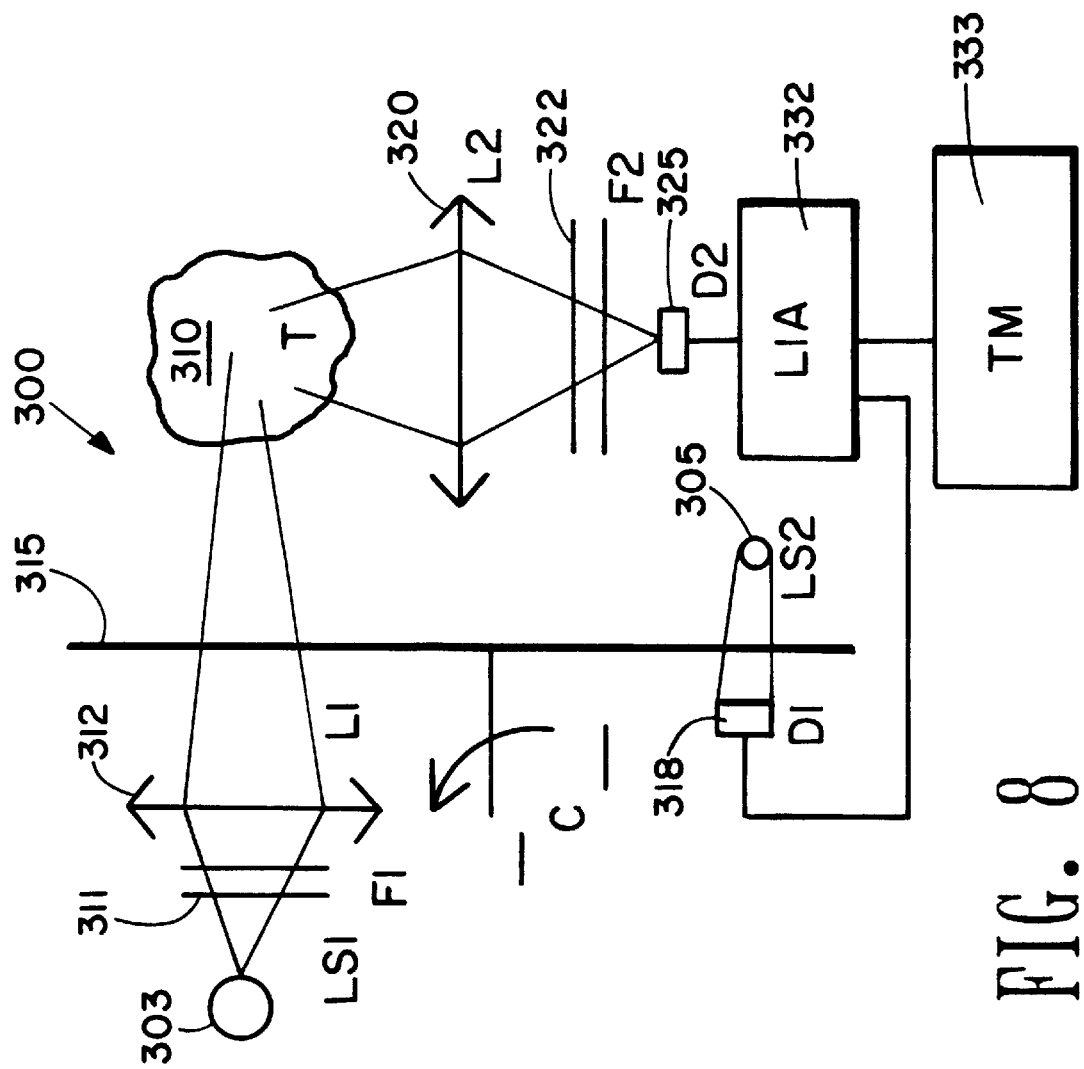
FIG. 8 is a schematic of one embodiment 300 of the present invention in which light sources 303 and 305 are utilized to analyze target 310 for contaminants.

Referring now to FIG. 8, there is shown a schematic for an apparatus 300 for detecting chicken fecal pollution in water environments. System 300 includes light source (LS1) 303 providing light to target (T) 310 throught filter (F1) 311 and lens (L1) 312. The light passes through modulator 315, a rotating chopper to produce a certain duty-cycle for passing light. Light fluorescing from target 310 passes through lens (L2) 320 and filter (F2) 322 to detector (D2) 325. System 300 also includes light source (LS2) 305 providing a reference light signal through modulator 315 to detector (D1) 318. Lock-in amplifier (LIA) 332 receives a signal and reference signal from both detectors 305 and 325, respectively, with output provided to terminal 333.

This system 300 can be built in a way that it is strictly sealed so that it can be immersed in a chilling-water tank of chicken processing plant or other water environment for monitoring the concentration of chicken fecal contaminant. A narrow band wavelength optical beam such as at wavelengths around 296 nm irradiate into the water, the signal within 320 nm to 470 nm from chicken fecal contaminants is amplified by a lock-in technology and then sent to the terminator(include detection and date processing system), D1 (318) and LS2 here are used as a reference for self-correlation detection.

According to another embodiment of the present invention, there is provided a method of matching sample specimens to a source. For example, the inventors have determined that chicken feces from different farms or processing plants showed some differences on their absorbent spectra over 210 nm to 500 nm and fluorescent spectra over 300 nm to 600 nm. Whereas, chicken feces from the same farm or plant demonstrated far more consistent absorbent spectrum and fluorescent spectrum within the 210 nm to 500 nm and 300 nm to 600 nm correspondingly. Without being limited to theory, the inventors believe that the fluorescence of chicken feces are very dependent upon the feed and other farm or plant conditions, which vary from farm to farm or plant. Thus, if a meat or poultry processor desired to identify the source of any particular meat or poultry sample, the fluoresce spectra of the sample could be compared to that of various known source spectra. While this method might not always provide a single source answer, it could be used to narrow down the source.

While the present invention has been illustrated as having chicken on a conveyor belt traverse in front of a stationary light transmitter 25, it is to be understood that the chicken could be stationary and light transmitter in motion, or both could be in motion.

While the present invention has been illustrated as having a light transmitter and receiver, it is to be understood that the present invention finds utility for enhancing human inspection of meat and poultry. For example, instead of a receiver, an inspector could monitor meat and poultry as it passed through inspection area 20. Additionally, the present invention could be incorporated into a hand-held or portable unit which could be utilized to inspect meat and poultry. Additionally, stationary units could be provided at points of sale for the peace of mind of the consumer to inspect meat or poultry immediately prior to purchase.

EXAMPLE

This example is provided merely to illustrate one embodiment of the present invention and is not to be used to limit the scope of the claims in any manner,

Collection and preparation of chicken feces

Twenty samples of fresh chicken feces were randomly collected from two Northwest Arkansas broiler processing plants and one Northwest Arkansas chicken farm, 5-g of each sample was suspended in 10 ml deionized water by vigorously shaking and then filtering through filter paper (#1, Norman Company). The filtrates were kept at 4° C. for not longer than two weeks before use. Different concentrations (g dry weight / ml ) of fecal suspensions were obtained by diluting the original filtrates with deionized water.

Absorption spectrum, excitation spectrum, and fluorescence spectrum of chicken feces filtrates The absorption spectrum of chicken feces filtrate (CFF) was scanned by using a spectrophotometer (8452A, HP Company). The measurement range was 190–850 nm and the resolution was 2 nm, The fluorescence spectra of CFF at interested excitation wavelengths were obtained by using a fluorescence spectrophotometer (650-40, Perking-Elmer Company). Both the excitation slit and the emission slit were 2 nm.

Fluorescence spectrum of chicken skin at selected excitation wavelengths

Figure 4:
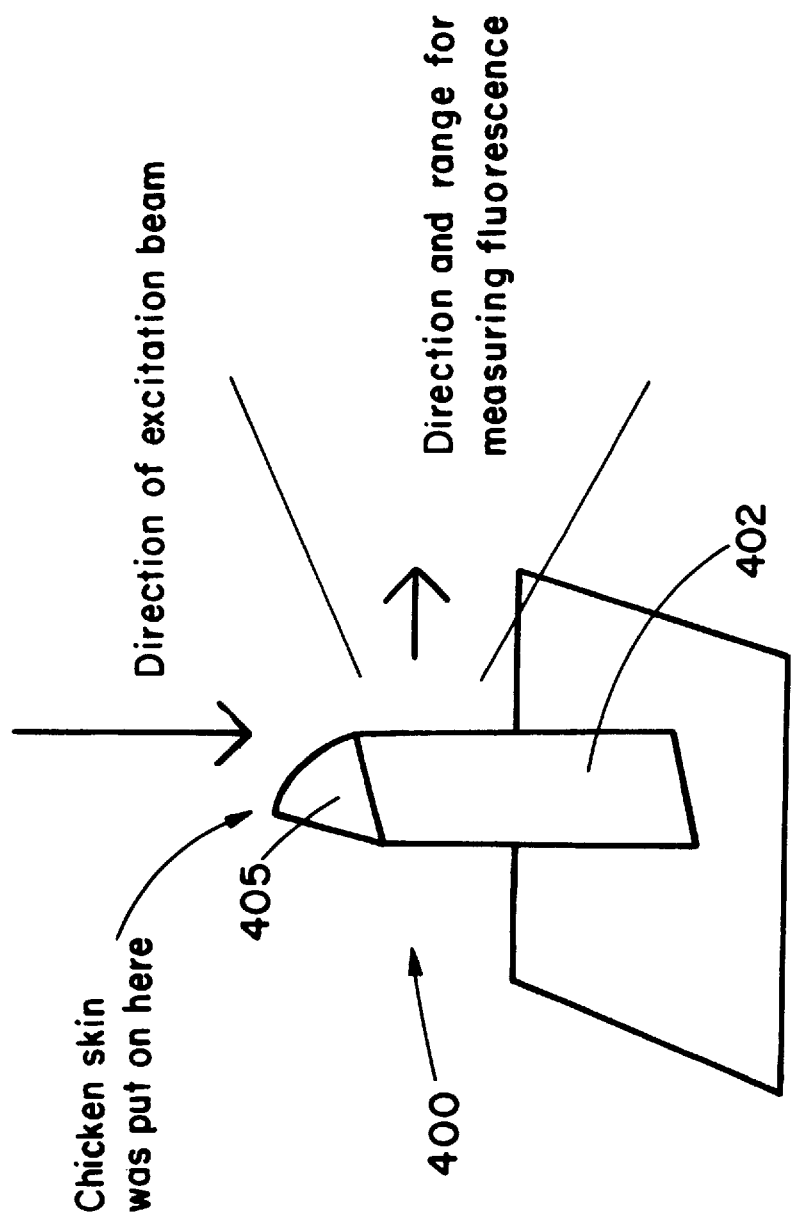
FIG. 4 is an illustration of sample holder 400 showing support member 402 and sample 405.

To obtain a suitable ratio of chicken fecal signal to chicken skin signal, investigation was conducted on the fluorescence spectrum of chicken skin at some selective excitation wavelengths. Pieces of chicken skin 405 (1×2 cm) randomly cut from chicken broiler carcasses were smoothly attached to support member 402 of a designed skin holder 400 as shown in FIG. 4., and then scanned. 10 samples were so processed. The excitation slit and emission slit were 2 nm.

The detection of chicken fecal contamination on chicken skin

Using the experimentally selected wavelengths such as 275 nm, 345 nm and etc., as a excitation wavelength, chicken skin and chicken feces will demonstrate, as shown in FIG. 3, not only the different spectral wavelengths but also the different ratios (contrast) of intensity of fluorescence. It is important to remember that optics property of chicken skin and chicken feces will vary from farm to farm and so does the excitation wavelength used and the resulting fluorescence spectra for detection. By scanning the excitation spectra and fluorescence spectra of chicken skin and chicken feces (water suspension), the optimal excitation wavelength and fluorescence wavelength for detection may be easily determined.

Referring now to FIG. 5, there is shown for a 275 nm excitation, the fluorescence spectra of chicken skin and feces water suspension ($3.9 \times 10^{-4}$ g dry weight/ml deionized water). The samples were inoculated by dropping the fecal solution on the skin for approximately 1 min. Next, the chicken skin was then washed by slow running deionized water for 30 seconds for three times. The spectrum of the inoculated chicken skin was scanned at every step of the treatments. As shown in FIG. 5, after the second wash the fluorescence intensity of chicken skin returned essentially to normal at the range of 340–400 nm.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

We claim:

1. A method for analyzing a consumable sample for the presence of contaminants, the method comprising:

(a) providing an excitation light having an excitation wavelength to the sample to produce sample fluorescence, wherein the light is suitable to excite the consumable and any contaminant to fluorescence at a measurement wavelength, and wherein at the measurement wavelength the ratio or difference between the contaminant fluorescence and the consumable fluoresence is suitable to allow determination of the presence of the contaminant;

(b) measuring the sample fluorescence at the measurement wavelength;

(c) comparing the sample fluorescence to consumable fluorescence at the measurement wavelength; and (d) producing a signal indicative of the presence of consumable fluorescence if the sample fluorescence is greater than the consumable fluorescence.

2. An apparatus for analyzing a consumable sample for the presence of contaminants, the apparatus:

(a) a light source positioned to provide an excitation light having an excitation wavelength to the sample to produce sample fluorescence, wherein the light is suitable to excite the consumable and any contaminant to fluorescence at a measurement wavelength, and wherein at the measurement wavelength the ratio or difference between the contaminant fluorescence and the consumable fluoresence is suitable to allow determination of the presence of the contaminant;

(b) a sample fluorescence detector positioned to receive sample fluorescence from the sample at the measurement wavelength;

(c) a comparison device for comparing the sample fluorescence to consumable fluorescence at the measurement wavelength; and (d) a signal generator producing a signal indicative of the presence of consumable fluorescence if the sample fluorescence is greater than the consumable fluorescence.

3. A method for analyzing a consumable sample for the presence of contaminants, the method comprising:

(a) providing an excitation light having an excitation wavelength to the consumable to produce a fluorescent spectrum for the consumable;

(b) providing the excitation light to the contaminant to produce a fluorescent spectrum for the contaminant;

(c) selecting a measurement wavelength from the fluorescent spectrum in steps (a) and (b) at which the ratio or difference between the contaminant fluorescence and the consumable fluoresence is suitable to allow determination of the presence of the contaminant;

(d) providing the excitation light to the sample to produce sample fluorescence;

(e) measuring the sample fluorescence at the measurement wavelength;

(f) comparing the sample fluorescence to consumable fluorescence at the measurement wavelength; and (g) producing a signal indicative of the presence of consumable fluorescence if the sample fluorescence is greater than the contaminant fluorescence.

4. A method for comparing a contaminated consumable sample to known controls, the method comprising:

(a) providing an excitation light having an excitation wavelength to the sample to produce sample fluorescence, wherein the light is suitable to excite the contaminant to fluorescence at a measurement wavelength;

(b) measuring the sample fluorescence at the measurement wavelength;

(c) comparing the sample fluorescence to fluorescence of two or more known controls; and (d) selecting the known control which in step (c) provided the closest comparision to identify the contaminant.

* * * * *